US012653463B2

(12) United States Patent　　　(10) Patent No.:　US 12,653,463 B2
Tiemann et al.　　　　　　　　　(45) Date of Patent:　Jun. 16, 2026

(54) MONITORING SYSTEM FOR A FEEDING BOTTLE

(71) Applicant: KONINKLIJKE PHILIPS N.V., Eindhoven (NL)

(72) Inventors: Christian Andreas Tiemann, Eindhoven (NL); Cornelis Bernardus Aloysius Wouters, Echt (NL); Łucja Elżbieta Segaar, Oirschot (NL); Renée Antoinette Otte, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1049 days.

(21) Appl. No.: 17/774,532

(22) PCT Filed: Nov. 6, 2020

(86) PCT No.: PCT/EP2020/081217
§ 371 (c)(1),
(2) Date: May 5, 2022

(87) PCT Pub. No.: WO2021/094201
PCT Pub. Date: May 20, 2021

(65) Prior Publication Data
US 2022/0401033 A1　　Dec. 22, 2022

(30) Foreign Application Priority Data
Nov. 12, 2019　(EP) ..................................... 19208578

(51) Int. Cl.
*A61B 5/00*　　　(2006.01)
*A61J 9/00*　　　(2006.01)

(52) U.S. Cl.
CPC ............... *A61B 5/6887* (2013.01); *A61J 9/00* (2013.01); *A61B 2562/0219* (2013.01); *A61J 2200/70* (2013.01)

(58) Field of Classification Search
CPC ............... A61J 9/00; A61B 2562/0219; A61B 2503/04; A61B 5/4205
See application file for complete search history.

(56) References Cited

U.S. PATENT DOCUMENTS 10,186,169 B2　1/2019　Lau
2015/0196247 A1*　7/2015　Lau .......................... G01F 1/363
　　　　　　　　　　　　　　　　　　　600/301
(Continued)

FOREIGN PATENT DOCUMENTS

CN　　204501708 U　　7/2015
CN　　204501717 U　　7/2015
(Continued)

OTHER PUBLICATIONS

International Search Report and Written Opinion Dated Feb. 4, 2021 For International Application No. PCT/EP2020/081217 Filed Nov. 6, 2020.
(Continued)

*Primary Examiner* — May A Abouelela
*Assistant Examiner* — Yasmeen S Warsi

(57) ABSTRACT

A monitoring system is provided for a feeding bottle, in particular a feeding bottle for feeding milk to a baby. Motion of the feeding bottle is sensed during feeding and a sucking performance is determined from the motion characteristics, in particular to identify whether the feeding is based on suckling or sucking.

20 Claims, 3 Drawing Sheets

(56) References Cited

U.S. PATENT DOCUMENTS

| | | | |
|---|---|---|---|
| 2015/0208979 A1 * | 7/2015 | Cunningham ......... | A61B 5/038 |
| | | | 600/590 |
| 2018/0197629 A1 * | 7/2018 | Zhou ..................... | G16H 20/60 |
| 2018/0220955 A1 | 8/2018 | Cunningham | |
| 2019/0298615 A1 | 10/2019 | Wood | |

FOREIGN PATENT DOCUMENTS

| | | | | |
|---|---|---|---|---|
| CN | 104997641 A | 10/2015 | | |
| CN | 205163676 U | 4/2016 | | |
| CN | 106598274 A | 4/2017 | | |
| CN | 104771320 B | 12/2017 | | |
| WO | WO-2009133492 A1 * | 11/2009 | ........... | A61B 5/6887 |

OTHER PUBLICATIONS

Arvedson, et al: "Pediatric Swallowing and Feeding: Assessment and Management", Cengage Learning, 2002, p. 56.
Shulman, et al: "Pediatric Speech and Language: Perspectives on Interprofessional Practice", Elsevier Health Sciences, 2018.
Fernando, et al: "Raising a healthy, happy eater: a parent's handbook—a stage-by-stage guide to setting your child on the path to adventurous eating", 2015 https://www.google.com/books/edition/Raising_a_Healthy_Happy_Eater_A_Parent_s/dVVVCQAAQBAJ?hl=en&gbpv=1&printsec=frontcover.
L. L. Overland, "A sensory motor approach to feeding", 2013.
Festila, et al: "Suckling and non-nutritive sucking habit: what should we know?", Clujul Medical 2014 vol. 87—No. 1.

* cited by examiner

MONITORING SYSTEM FOR A FEEDING BOTTLE

CROSS REFERENCE TO RELATED APPLICATIONS

This application is the U.S. National Phase application under 35 U.S.C. § 371 of International Application No. PCT/EP2020/081217 filed Nov. 6, 2020, which claims the benefit of European Patent Application Number 19208578.5 filed Nov. 12, 2019. These applications are hereby incorporated by reference herein.

FIELD OF THE INVENTION

This invention relates to feeding bottles and in particular relates to a system for monitoring the drinking performance of an infant when drinking from a bottle.

BACKGROUND OF THE INVENTION

It is desirable when bottle feeding a baby to know how well the baby is drinking. It is known to monitor drinking performance and to provide feedback to the parent. One known example is in the form of a sleeve for the baby bottle, which incorporates a load cell, for measuring the weight of the milk contained by the bottle before and after feeding, and thereby to calculate the milk volume consumed by the infant. The sleeve also contains an accelerometer, to give feedback to the parents in respect of the correct bottle angle, as well as for monitoring the drinking behavior of the child by looking at the bottle movements (e.g., to identify drinking bursts and pauses). The system also allows data to be sent to a companion app for analysis and visualization.

This drinking performance evolves over time. In particular, two different patterns of the sucking action occur during infant development. These two different patterns are termed "suckling" and "sucking".

Suckling is the first pattern, which gradually develops during the 2nd and 3rd trimester of pregnancy. It involves a front to back movement of the tongue, with the backward motion more pronounced. There is jaw motion up and down. The tongue does not protrude beyond the lips. Liquid is extracted from a breast or bottle through rhythmic tongue movements combined with pronounced opening and closing of the jaw. The seal of the lips around the nipple or teat may be loose. Suckling is highly automatic and reflexive. It activates a high number of muscles and is therefore important in an infant's facial growth.

By four months of age, the reflexive suckling gradually disappears and drinking becomes more voluntary. The suckling reflex may persist until 6 months of age, after which a more mature sucking pattern emerges.

During sucking, the body of the tongue raises and lowers with strong activity of its intrinsic muscles, and therefore the jaw makes smaller up-down motions. There is also a firmer sealing of the lips. The strength of lip closure is a major factor in the shift of tongue patterns from an in-out to an up-down direction.

Thus, differences between suckling and sucking for example relate to the tongue movement direction (in-out during suckling and up-down during sucking), the range of tongue movement, differences in jaw motion, and the strength of lip closure.

It would be desirable to be able to monitor the drinking characteristics or performance of a baby, in particular to assess the maturity of the sucking ability, rather than only the overall quantity or flow rate during drinking.

SUMMARY OF THE INVENTION

The invention is defined by the claims.

According to examples in accordance with an aspect of the invention, there is provided a monitoring system for a feeding bottle, comprising:

a motion sensor for sensing motion of the feeding bottle during feeding; and a processor adapted to identify from the motion sensor signals a sucking performance, wherein the sucking performance identifies whether the feeding is based on suckling or sucking; and an output interface for providing sucking performance information.

The invention thus provides a system which determines the sucking performance during feeding. Monitoring the presence (or absence) of suckling and sucking patterns provides relevant information for parents and professionals. In particular, it enables parents to follow the transition from suckling to sucking, and to detect in an early phase if issues may occur and special attention is needed, e.g., related to pacifier and nippy cup usage.

Issues with feeding (managing thicker liquids and soft foods) and speech may occur if the suckling to sucking transition is not progressing appropriately. The system thus provides objective data to parents regarding the oral development of their baby, which is also very helpful because it can be difficult for parents to visually differentiate between suckling and sucking.

The sucking performance information may identify a progression stage between suckling and sucking. In a most simple implementation, there is simply binary discrimination between suckling and sucking. In a refinement, a stage of progression may be determined. For example, an analog value may for example be provided, such as in a range from 0 to 1, with one extreme representing sucking and the other representing suckling.

The motion sensor for example comprises a three-axis motion sensor. This enables all movements of the bottle to be taken into account.

The motion sensor for example comprises a three-axis accelerometer and/or a three-axis gyroscope. Linear movements and rotational movements may be of interest and multiple sensor types may be used to capture all relevant motion information.

The output interface for example comprises a wireless transmitter for sending the sucking performance information to a remote device for presentation to a user. The remote device may for example be a mobile phone or tablet on which a suitable app has been loaded.

The processor may be adapted to:

convert time-domain motion sensor signals into the frequency domain;

perform spectral density analysis;

determine signal powers in a frequency range corresponding to a sucking frequency; and analyze the signal powers to identify the sucking performance.

This is one possible processing method, using frequency domain analysis.

In another example, the processor is adapted to:

perform detection of peaks of the time-domain motion sensor signals;

derive features of the detected peaks; and analyze the features to identify the sucking performance.

This is another possible processing method, using time domain analysis.

The monitoring system may be arranged as a sleeve for mounting around a feeding bottle. The user may then simply insert the bottle into the sleeve to enable the feeding performance to be monitored during feeding.

The invention also provides a feeding bottle system, comprising:

a feeding bottle; and a monitoring system as defined above for monitoring the sucking performance during feeding.

The invention also provides a method for monitoring sucking performance during feeding from a feeding bottle, comprising:

sensing motion of the feeding bottle during feeding to generate motion sensing signals;

identifying, from the motion sensing signals, a sucking performance, wherein the sucking performance identifies whether the feeding is based on suckling or sucking; and outputting sucking performance information.

The sucking performance for example identifies a progression stage between suckling and sucking. Sensing motion preferably comprises a three-axis motion sensing.

In one example, the method comprises:

converting time-domain motion sensor signals into the frequency domain;

performing spectral density analysis;

determining signal powers in a frequency range corresponding to a sucking frequency; and analyzing the signal powers to identify the sucking performance.

In another example, the method comprises:

performing detection of peaks of time-domain motion sensor signals;

deriving features of the detected peaks; and analyzing the features to identify the sucking performance.

The invention also provides a computer program comprising computer program code means which is adapted, when said program is run on a computer, to implement the method defined above.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
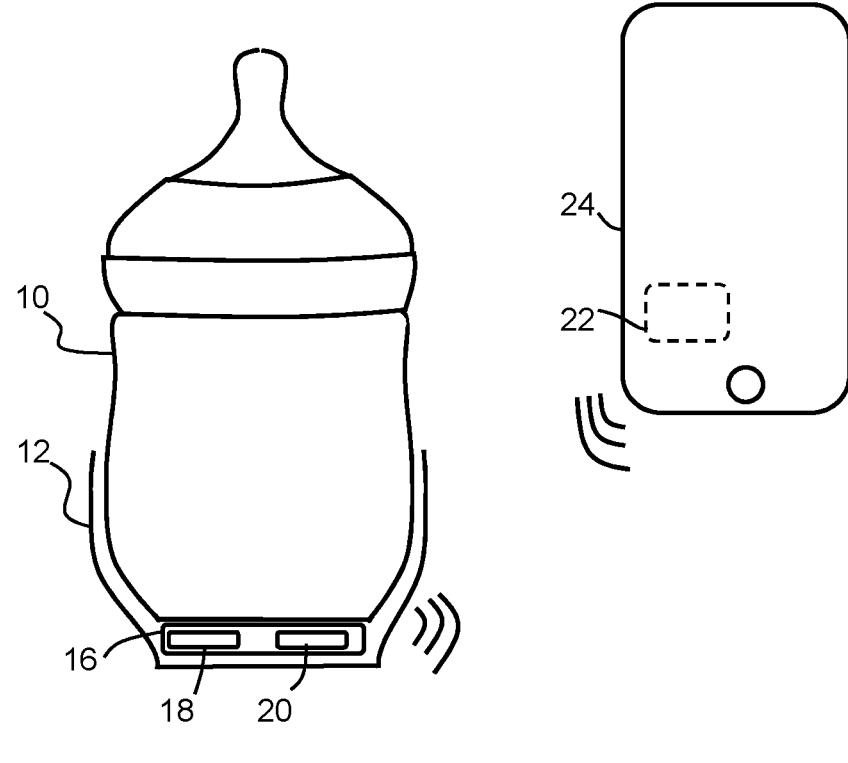
FIG. 1 shows a feeding bottle mounted in a sleeve which functions as a monitoring system.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a monitoring system for a feeding bottle, in particular a feeding bottle for feeding milk to a baby. Motion of the feeding bottle is sensed during feeding and a sucking performance is determined from the motion characteristics, in particular to identify whether the feeding is based on suckling or sucking.

FIG. 1 shows a feeding bottle 10 mounted in a sleeve 12 which functions as a monitoring system. The sleeve 12 surrounds the feeding bottle 10.

A monitoring unit 16 is in this example provided in the base of the sleeve 12, and comprises a motion sensor 18, and an output interface 20. The monitoring unit 16 may be incorporated anywhere in or on the sleeve.

The base part of the sleeve for example also includes a battery, and optionally means for providing visual feedback to the user via LEDs. The output interface 20 may comprise this LED arrangement. However, a preferred implementation instead (or additionally) has an output interface which communicates the results wirelessly to a smartphone 24 or tablet as shown.

A processor 22 determines a sucking performance for the feeding baby based on the sensed motion.

In the example shown, the processor 22 is the processor of a mobile phone 24 which communicates wirelessly with the monitoring unit 16. Thus, the sleeve locally detects motion, and the remote processor analyzes the motion to derive the sucking performance information. Thus, a parent feeding a baby may monitor on their mobile phone how the sucking performance of the baby is evolving. This is of course only one example. The processor 22 which analyses the motion data could also be located on the sleeve and integrated with the monitoring unit 16. In this case only the output (drinking performance) needs to be transmitted to the mobile phone. In this case, raw motion data does not have to be transmitted to the phone, saving time and battery life.

The motion sensor 18 preferably comprises a 3-axis acceleration sensor and/or a 3-axis gyroscope.

Figure 2:
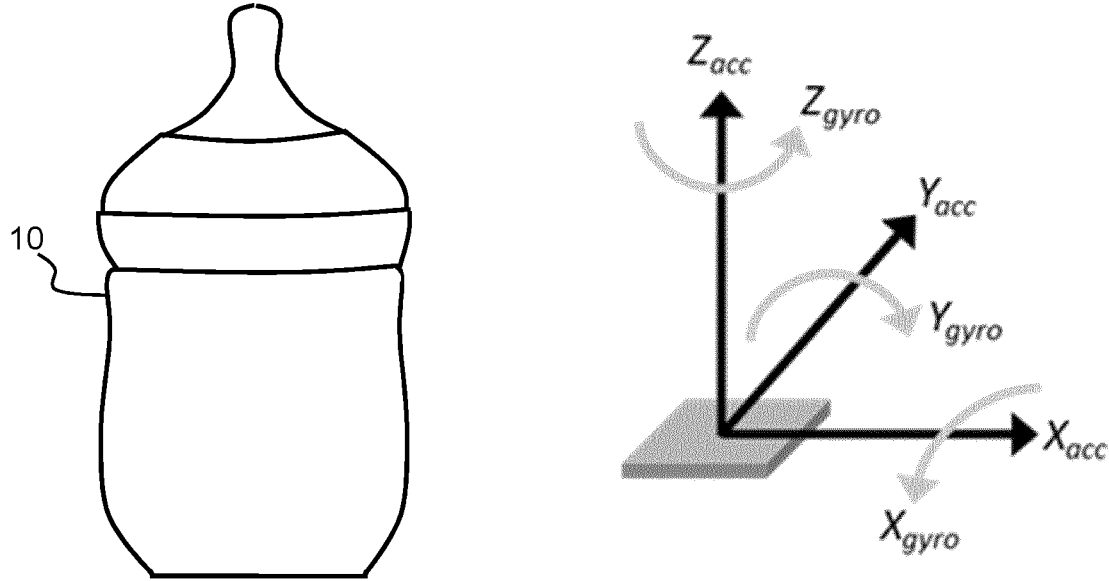
FIG. 2 shows one possible set of signals from a combination of a 3-axis acceleration sensor and a 3-axis gyroscope.

FIG. 2 shows one possible set of signals from a combination of a 3-axis acceleration sensor and a 3-axis gyroscope. An image of the bottle 10 is shown to illustrate the 3-axis orientations.

This arrangement gives three linear acceleration signals Xacc, Yacc, Zacc and three angular velocity signals Xgyro, Ygyro and Zgyro. The motion sensor is generally an inertia measurement unit and/or force or acceleration measurement unit.

The processor 22 is programmed to determine the presence of suckling and/or sucking during a feed. It can furthermore monitor drinking patterns over time to provide objective feedback regarding the suckling and sucking status of a baby, and to indicate if issues may occur and special attention is needed, e.g., related to pacifier and nippy cup usage.

As mentioned above, suckling involves a front to back movement of the tongue with the backward motion more pronounced. This will result in a motion along the longitudinal axis of the bottle, i.e., the z-component of the accelerometer (Zacc in FIG. 2). A higher acceleration magnitude is therefore expected in this direction compared to the other directions, Xacc and Yacc. In case the backward motion is more pronounced, the acceleration magnitude will be higher in the minus Zacc direction compared to the positive Zacc direction. Furthermore, the acceleration will follow a cyclic pattern linked to the suckling frequency which is typically between 1 Hz and 2 Hz.

During suckling, the seal of the lips around the teat is loose and there is a pronounced opening and closing of the jaw. Because parents typically hold the bottle at the bottom, the position of the bottom part is relatively fixed. The opening and closing of the jaw may therefore induce an angular cyclic motion of the bottle, which can be measured using the gyroscope, in particular the Xgyro and Ygyro signals.

During sucking, the jaw movements are less pronounced and there is strong activity of the intrinsic muscles, such that the angular motion of the bottle is less pronounced.

Thus, the main differentiator between sucking and suckling is the amount of front to back linear movement along the z axis, as well as an amount of rocking about the x or y axis. These types of movement are less present during sucking compared to suckling.

Figure 3:
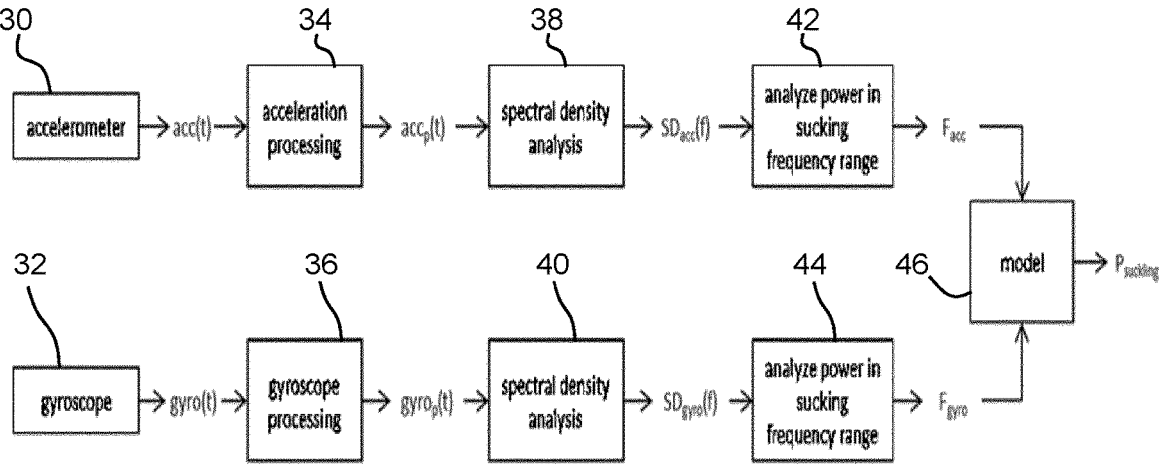
FIG. 3 shows a first example of a processing algorithm carried out by the processor.

FIG. 3 shows a first example of a processing algorithm carried out by the processor 22 to detect these differences, and based on a frequency-domain approach.

An accelerometer 30 generates accelerometer signal acc (t) and a gyroscope 32 generates gyroscope signal gyro(t) during a feed. Typically, the sensors perform measurements in 3 directions. Hence, the signals are 3-dimensional.

In a next step, acc(t) and gyro(t) are processed by processing units 34, 36 to remove gravity-induced offsets and noise. Depending on the orientation of the sensors on the bottle, the 3 dimensional signals also need to be adjusted, e.g., using a rotation matrix. Subsequently, motions in the desired directions explained above can be extracted, which are denoted by accp(t) and gyrop(t).

Next a spectral density analysis is performed on accp(t) and gyrop(t) by spectral analysis units 38, 40, resulting in power spectra SDacc(f) and SDgyro (f) describing the power of the signals as function of frequency f.

The powers of the signals in the sucking frequency range (1 Hz to 2 Hz) are derived from the power spectra. A relatively high power is expected in this frequency range if suckling drinking behavior is present. Multiple features which are potentially informative for suckling behavior can be derived from the power spectra in feature analysis units 42, 44 such as absolute power, relative power, and morphology metrics. The collections of features are denoted by Facc and Fgyro.

These features are used to determine if suckling behavior is present in the feed.

One option is to use a logistic regression model 46 which generates a value between 0 and 1, indicating the probability Psuckling of suckling being present, or indicating the relative presence of suckling behavior. Other modeling techniques can be used as well. For instance, a decision graph can be developed to determine if suckling behavior is present.

The spectral density analysis thus assesses the power of the relevant acceleration signals in the frequency range of interest. An increased spectral density is expected in this frequency range, which will decrease over time when suckling is replaced by sucking.

Figure 4:
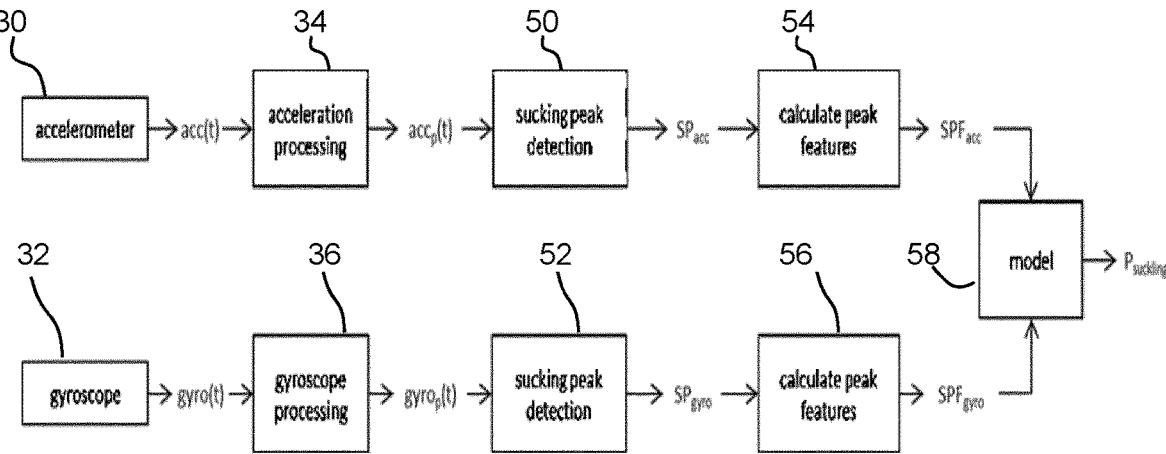
FIG. 4 shows a second example of a processing algorithm carried out by the processor.

FIG. 4 shows an alternative time-domain approach, also for the real-time detection of suckling behavior. The initial processing steps 34, 36 are identical to FIG. 3. Instead of performing a spectral analysis, a peak detection method is applied by peak detection units 50, 52 in the time-domain to identify peaks related to sucking/suckling.

Subsequently, multiple features are calculated from the identified peaks using peak analysis units 54, 56, e.g., peak magnitude, peak slope, peak duration, peak minimum, etc.

These features can be used in a model 58 to determine the presence of suckling behavior.

In an alternative approach, templates may be defined for expected acceleration and gyroscope profiles during suckling, and template matching techniques may then be used to determine if suckling is present.

In the above approaches there is an accelerometer branch and a gyroscope branch, which in the end come together as inputs for the model 46, 58 to identify the presence of suckling behavior. In principle, a single branch (e.g., only based on the accelerometer or gyroscope) could be used as well. However, by combining information from both sensor types, the accuracy of the final output is higher.

Figures 5, 6:
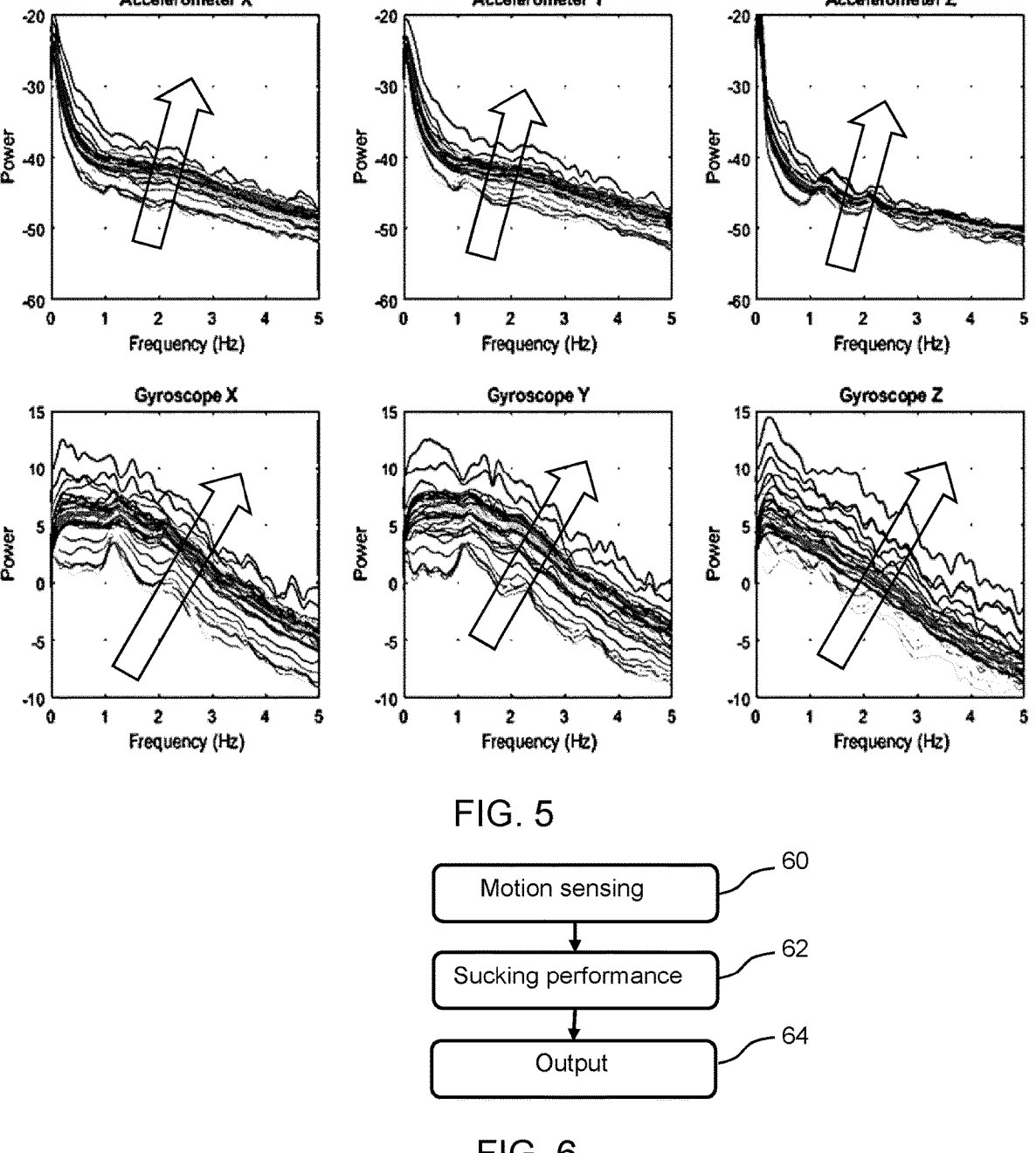
FIG. 5 shows signals from the six sensors of FIG. 2 as moving averages of spectral densities during bottle feedings, during a period of 6 months when the baby's age increases from 2 months to 8 months.
FIG. 6 shows a method for monitoring sucking performance during feeding from a feeding bottle.

FIG. 5 shows signals from the six sensors of FIG. 2 as moving averages of spectral densities during bottle feedings, during a period of 6 months when the baby's age increases from 2 months to 8 months.

At 2 months age the suckling behavior is expected regularly. Towards the end of the study, at an age of 8 months, the introduction of sucking behavior is expected. For each feed, the spectral density was calculated for the accelerometer and gyroscope signals.

Each line in FIG. 5 represents a different age, from month 2 to month 8. The arrows show how the plots progress from 2 months to 8 months.

During the initial phase of the study, a peak in spectral power can be observed around 1.2 Hz (corresponding to the suckling frequency) in the z-component of the accelerometer and in the x- and y-components of the gyroscope. When the baby becomes older the total power in all frequencies increases, indicating that the movement becomes stronger over time. However, the clear peaks around the suckling/sucking frequency gradually disappear.

This shows that the spectral density information is able to distinguish between sucking and suckling. The spectral information may be used as input for a classifier to estimate the probability the bottle movement comes from suckling or sucking. Examples of techniques include clustering, logistic regression, and neural networks.

In the example above, some processing takes place in the remote device via an app. Of course, the system may instead be fully integrated into the sleeve. Alternatively, some processing may performed even more remotely—for example the mobile telephone may send data to an external host for processing, and the results are then returned.

The example above is based on the use of a sleeve around the bottle. There are alternative implementations, such as sensors integrated in the teat, or in a ring below the teat.

FIG. 6 shows a method for monitoring sucking performance during feeding from a feeding bottle.

In step 60 the motion of the feeding bottle during feeding is sensed to generate motion sensing signals.

In step 62, a sucking performance is identified, from the motion sensing signals. It identifies whether the feeding is based on suckling or sucking.

The sucking performance information is output in step 64.

As discussed above, the system makes use of processor to perform the data processing. The processor can be implemented in numerous ways, with software and/or hardware, to perform the various functions required. The processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A monitoring system for a feeding bottle, the monitoring system comprising:

at least one three-axis motion sensor for sensing motion of the feeding bottle during feeding, and generating motion sensor signals indicating the sensed motion, the motion sensor signals comprising linear acceleration signals and angular velocity signals corresponding to three axes, respectively; and a processor for determining in real-time from the motion sensor signals whether the feeding is based on sucking or suckling, and outputting sucking performance information indicating whether the feeding is based on the sucking or suckling; and an output interface for enabling display of the sucking performance information identifying whether the feeding is based on the sucking or suckling to enable monitoring of drinking performance.

2. The monitoring system as claimed in claim 1, wherein the sucking performance information identifies a progression stage between the suckling and sucking.

3. The monitoring system as claimed in claim 1, wherein the at least one three-axis motion sensor comprises a three-axis accelerometer and/or a three-axis gyroscope.

4. The monitoring system as claimed in claim 1, wherein the output interface comprises a wireless transmitter for sending the sucking performance information to a remote device for presentation to a user.

5. The monitoring system as claimed in claim 1, wherein the processor determining whether the feeding is based on the sucking or suckling comprises:

converting time-domain motion sensor signals into a-frequency domain motion sensor signals;

performing spectral density analysis on the frequency domain motion sensor signals resulting in power spectra;

determining signal powers in a frequency range corresponding to a sucking frequency from the power spectra; and analyzing the signal powers to identify sucking performance.

6. The monitoring system as claimed in claim 1, wherein the processor determining whether the feeding is based on the sucking or suckling comprises:

performing a detection of peaks of time-domain motion sensor signals;

deriving features of the detected peaks; and analyzing the features to identify sucking performance.

7. The monitoring system as claimed in claim 1, wherein the monitoring system is arranged as a sleeve for mounting around the feeding bottle.

8. A feeding bottle system, comprising:

the feeding bottle; and the monitoring system as claimed in claim 1 for monitoring sucking performance during feeding from the feeding bottle.

9. The monitoring system as claimed in claim 2, wherein the sucking performance information identifies the progression stage between the suckling and sucking by providing an analog value a range between first and second extremes, wherein the first extreme represents the sucking and the second extreme represents the suckling.

10. A method for monitoring sucking performance during feeding from a feeding bottle, the method comprising:

sensing motion of the feeding bottle during feeding using at least one three-axis motion sensor to generate motion sensing signals;

generating motion sensor signals indicating the sensed motion, the motion sensor signals comprising linear acceleration signals and angular velocity signals corresponding to three axes, respectively;

determining in real-time, from the motion sensing signals, whether the feeding is based on suckling or sucking; and displaying sucking performance information indicating whether the feeding is based on the suckling or sucking; and monitoring of drinking performance based on the sucking performance information.

11. The method as claimed in claim 10, wherein the sucking performance information identifies a progression stage between the suckling and sucking.

12. The method as claimed in claim 10, wherein the at least one three-axis motion sensor comprises three-axis accelerometer and/or a three-axis gyroscope.

13. The method as claimed in claim 10, wherein determining whether the feeding is based on the sucking or suckling comprises:

converting time-domain motion sensor signals into a frequency domain signal;

performing spectral density analysis on the frequency domain signal resulting in power spectra;

determining signal powers in a frequency range corresponding to a sucking frequency from the power spectra; and analyzing the signal powers to identify sucking performance.

14. The method as claimed in claim 10, wherein determining whether the feeding is based on the sucking or suckling comprises:

performing detection of peaks of time-domain motion sensor signals;

deriving features of the detected peaks; and analyzing the features to identify sucking performance.

15. A non-transitory computer readable medium storing instructions for monitoring sucking performance during feeding from a feeding bottle that, when run on a computer, cause the computer to:

receive motion sensing signals from at least one three-axis motion sensor indicating sensed motion of the feeding bottle during feeding;

generate motion sensor signals indicating the sensed motion, the motion sensor signals comprising linear acceleration signals and angular velocity signals corresponding to three axes, respectively;

determine in real-time, from the motion sensing signals, whether the feeding is based on suckling or sucking; and output sucking performance information for display indicating whether the feeding is based on the suckling or sucking to enable monitoring of drinking performance.

16. The non-transitory computer readable medium as claimed in claim 15, wherein the sucking performance information identifies a progression stage between the suckling and sucking.

17. The non-transitory computer readable medium as claimed in claim 15, wherein the at least one three-axis motion sensor comprises a three-axis accelerometer and/or a three-axis gyroscope.

18. The non-transitory computer readable medium as claimed in claim 15, wherein the instructions cause the computer to output the sucking performance information to a remote device via a wireless transmitter for presentation to a user.

19. The non-transitory computer readable medium as claimed in claim 15, wherein the instructions cause the computer to determine whether the feeding is based on the sucking or suckling by:

converting time-domain motion sensor signals into frequency domain motion sensor signals;

performing spectral density analysis on the frequency domain motion sensor signals resulting in power spectra;

determining signal powers in a frequency range corresponding to a sucking frequency from the power spectra; and analyzing the signal powers to identify sucking performance.

20. The non-transitory computer readable medium as claimed in claim 15, wherein the instructions cause the computer to determine whether the feeding is based on the sucking or suckling by:

performing a detection of peaks of time-domain motion sensor signals;

deriving features of the detected peaks; and analyzing the features to identify sucking performance.

* * * * *